United States Patent
Gray et al.

(10) Patent No.: US 10,413,656 B2
(45) Date of Patent: Sep. 17, 2019

(54) FLUID DELIVERY MANAGEMENT IN A FLUID DELIVERY NETWORK

(71) Applicant: IVENIX, INC., Amesbury, MA (US)

(72) Inventors: George W. Gray, North Andover, MA (US); William C. McQuaid, Melrose, MA (US); Jesse E. Ambrosina, Topsfield, MA (US)

(73) Assignee: Ivenix, Inc., North Andover, MA (US)

( * ) Notice: Subject to any disclaimer, the term of this patent is extended or adjusted under 35 U.S.C. 154(b) by 0 days.

(21) Appl. No.: 15/420,416

(22) Filed: Jan. 31, 2017

(65) Prior Publication Data

US 2017/0136176 A1     May 18, 2017

Related U.S. Application Data

(63) Continuation of application No. 14/172,130, filed on Feb. 4, 2014, now Pat. No. 9,649,431.
(Continued)

(51) Int. Cl.
*A61M 5/00* (2006.01)
*A61M 5/142* (2006.01)
(Continued)

(52) U.S. Cl.
CPC .......... *A61M 5/142* (2013.01); *G06F 19/3418* (2013.01); *G06F 19/3468* (2013.01); *G06Q 50/24* (2013.01); *A61M 2205/3553* (2013.01); *A61M 2205/3584* (2013.01); *A61M 2205/502* (2013.01); *A61M 2205/6009* (2013.01)

(58) Field of Classification Search
CPC ...... A61M 2205/50; A61M 2205/6018; A61M 2205/6072; A61M 2205/3553; A61M 2205/3584; A61M 2205/6009; G06F 19/3468; G06F 19/3412; G06Q 50/22; G06Q 50/24
See application file for complete search history.

(56) References Cited

U.S. PATENT DOCUMENTS

| 5,429,602 A | 7/1995 | Hauser |
| 5,781,442 A | 7/1998 | Engleson |

(Continued)

FOREIGN PATENT DOCUMENTS

| JP | 2006155068 A | 6/2006 |
| JP | 2010266980 A | 11/2010 |

(Continued)

OTHER PUBLICATIONS

Extended European Search Report for EP14749474.4, dated Jan. 18, 2016; 10 pages.
(Continued)

*Primary Examiner* — William R Carpenter
(74) *Attorney, Agent, or Firm* — Armis IP Law, LLC

(57) ABSTRACT

An infusion management system includes an infusion management server configured for providing an order to an infusion device to administer an infusion and the infusion device. The infusion device may be configured for receiving the order, associating the order with a patient, and adjusting at least one setting according to the order. A method for administering an infusion, an interface for an infusion device and a computer program product are also disclosed.

11 Claims, 3 Drawing Sheets

Related U.S. Application Data

(60) Provisional application No. 61/761,126, filed on Feb. 5, 2013, provisional application No. 61/761,119, filed on Feb. 5, 2013.

(51) Int. Cl.
  G06Q 50/24 (2012.01)
  G06F 19/00 (2018.01)

(56) References Cited

U.S. PATENT DOCUMENTS

| | | | |
|---|---|---|---|
| 6,671,563 B1 | 12/2003 | Engleson | |
| 6,731,989 B2 | 5/2004 | Engleson | |
| 6,915,170 B2 | 7/2005 | Engleson | |
| 7,096,072 B2 | 8/2006 | Engleson | |
| 7,103,419 B2 | 9/2006 | Engleson | |
| 7,107,106 B2 | 9/2006 | Engleson | |
| 7,117,041 B2 | 10/2006 | Engleson | |
| 7,171,277 B2 | 1/2007 | Engleson | |
| 7,398,183 B2 | 7/2008 | Holland et al. | |
| 7,454,314 B2 | 11/2008 | Holland et al. | |
| 7,483,756 B2 | 1/2009 | Engleson | |
| 7,895,053 B2 | 2/2011 | Holland et al. | |
| 8,737,195 B2 | 5/2014 | Ohashi | |
| 8,858,526 B2 | 10/2014 | Bloomquist | |
| 2002/0126036 A1 | 9/2002 | Flaherty et al. | |
| 2003/0040700 A1 | 2/2003 | Hickle et al. | |
| 2003/0060765 A1 | 3/2003 | Campbell et al. | |
| 2003/0135388 A1 | 7/2003 | Martucci et al. | |
| 2003/0139701 A1 | 7/2003 | White et al. | |
| 2004/0167465 A1 | 8/2004 | Mihai et al. | |
| 2004/0176984 A1 | 9/2004 | White et al. | |
| 2004/0181314 A1 | 9/2004 | Zaleski | |
| 2006/0089539 A1 | 4/2006 | Miodownik et al. | |
| 2006/0116639 A1 | 6/2006 | Russell | |
| 2006/0200369 A1* | 9/2006 | Batch | A61M 5/16827 705/3 |
| 2006/0258985 A1 | 11/2006 | Russell | |
| 2007/0233520 A1 | 10/2007 | Wehba et al. | |
| 2008/0033402 A1* | 2/2008 | Blomquist | G06F 19/3456 604/890.1 |
| 2011/0238032 A1* | 9/2011 | McTaggart | G06F 19/3468 604/500 |
| 2011/0313789 A1 | 12/2011 | Kamen et al. | |
| 2012/0135764 A1 | 5/2012 | Ohashi | |

FOREIGN PATENT DOCUMENTS

| | | |
|---|---|---|
| WO | 2006016952 A2 | 2/2006 |
| WO | 2007126948 A2 | 11/2007 |

OTHER PUBLICATIONS

International Search Report for PCT/US2014/014588 dated May 20, 2014; 4 pages.

* cited by examiner

FLUID DELIVERY MANAGEMENT IN A FLUID DELIVERY NETWORK

RELATED APPLICATIONS

This application is a continuation application of U.S. patent application Ser. No. 14/172,130 entitled "AUTOMATED PROGRAMMING OF INFUSION THERAPY," filed on Feb. 4, 2014, the entire teachings of which are incorporated herein by this reference.

U.S. patent application Ser. No. 14/172,130 claims the benefit of U.S. Provisional Patent Application Ser. No. 61/761,126 entitled "Automated Programming of Infusion Therapy through Information Association," filed on Feb. 5, 2013, the entire teachings of which are incorporated herein by this reference.

U.S. patent application Ser. No. 14/172,130 claims the benefit of U.S. Provisional Patent Application Ser. No. 61/761,119 entitled "Clinical Association Server," filed on Feb. 5, 2013, the entire teachings of which are incorporated herein by this reference.

U.S. patent application Ser. No. 14/172,130 is related to U.S. patent application Ser. No., Ser. No. 14/172,048, entitled "Medical Device Management Using Associations," filed on Feb. 4, 2014, the entire teachings of which are incorporated herein by this reference.

BACKGROUND OF THE INVENTION

1. Field of the Invention

The invention disclosed herein relates to dispensing medication to a patient, and in particular to systems for infusing a patient with medication.

2. Description of the Related Art

A long-standing practice of healthcare providers has been to infuse patients with medication. Intravenous supply of fluids, such as saline solution, have provide for stabilizing the health of a patient. In conjunction with intravenous supply of fluids, healthcare providers very often include other medication, such as antibiotic. In fact, healthcare providers provide a myriad of different agents to patients in this manner. Accordingly, there is a substantial complement of equipment available to healthcare providers to facilitate infusing patients with medication.

Generally, an infusion device (also referred to herein as a "pump" and by other similar terms) is set up and programmed by a caregiver. That is, once a caregiver has coupled the proper medication the caregiver will then review the medication orders and manually program the device in order to dispense the medication.

As one might imagine, such processes can be time-consuming and provide many opportunities for human error. In an increasingly busy environment, such tools are cumbersome and can present genuine liability to the providers.

What are needed are methods and apparatus for improving infusion of medication for a patient. Preferably, the methods and apparatus provide for fewer user interactions and thus lower occurrence of medication errors.

SUMMARY OF THE INVENTION

In one embodiment, an infusion management system is disclosed. The system includes an infusion management server configured for providing an order to an infusion device to administer an infusion; and the infusion device, wherein the infusion device is configured for receiving the order, associating the order with a patient, and adjusting at least one setting according to the order.

In another embodiment, a method for administering an infusion is provided. The method includes selecting an infusion device that is in communication with an infusion management system; associating the infusion device with a patient; receiving at least one order for the patient from the infusion management system; and, initiating the administration according to the at least one order.

In yet another embodiment, an interface for an infusion device is provided. The interface includes a controller configured for communicating with and controlling the infusion device; a user interface configured for coupling with the controller and receiving user input; and at least one port for communicating with an infusion management system; wherein the infusion management system includes an infusion management server configured for providing an order to the infusion device to administer an infusion; and the controller is configured for receiving the order, associating the order with a patient, and adjusting at least one setting of the infusion device according to the order.

In a further embodiment, a computer program product is provided. The computer program product includes machine executable instructions stored on machine readable media. The product is configured for controlling an infusion device by executing a method that includes receiving an order object from an infusion management server, the order object including information for dispensing medication; adjusting the infusion device according to the order object; and administering the infusion.

BRIEF DESCRIPTION OF THE DRAWINGS

The features and advantages of the invention are apparent from the following description taken in conjunction with the accompanying drawings in which.

DETAILED DESCRIPTION OF THE INVENTION

Figure 1:
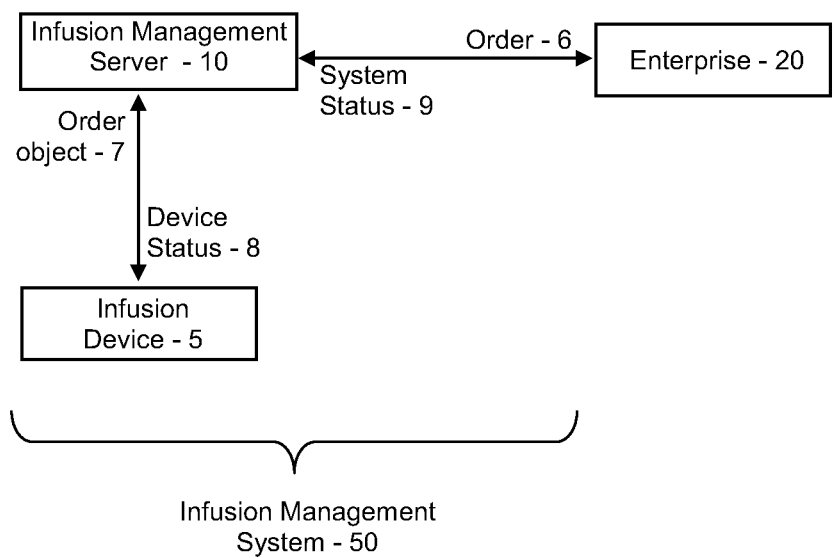
FIG. 1 is a flow diagram depicting aspects of an infusion management system according to the teachings herein.

Disclosed herein is an infusion management system for managing infusions of medications to patients in a healthcare setting. Generally, the methods and apparatus disclosed provide "smart" technologies that make use of substantial patient information, monitor processes, and pass information (such as status information) in order to keep caregivers informed and to simplify medical administration as well as system administration.

The infusion management system generally includes an infusion management server that is in communication with at least one and more often a plurality of infusion devices. The infusion management server provides enhanced functionality and control over each one of the infusion devices.

Embodiments of the infusion management system provide for automatically programming an infusion device to deliver a highly controllable infusion of medication. Embodiments herein may include using patient medication orders acquired from order entry and pharmacy information systems within the healthcare enterprise and providing those orders as order objects to an infusion device. Embodiments herein provide for automatically programming of the infusion device using information contained in the selected order.

Generally, the infusion management server (IMS) includes components deemed appropriate for performing the functions described herein. Some of the components that may be appropriately relied upon or a part of the infusion management server (IMS) are described below (see FIG. 3). Embodiments of the infusion management server (IMS) are not to be limited by those embodiments disclosed herein, and may include (or exclude, as appropriate) components and aspects known to those skilled in the art for performing the functions described and/or claimed herein. More specifically, components used in any specific embodiment of the infusion management server (IMS) are limited only by the needs and/or resources available to a respective user, designer, owner, manufacturer or other similarly interested party.

As an overview, in some embodiments, the infusion management server (IMS) includes a computer server through which medication orders are acquired from an enterprise (such as a hospital or other health care environment). The orders may be obtained electronically and/or submitted manually. In some embodiments, the orders are then stored on the infusion management server (IMS) and managed through their entire lifecycle. In addition, associations between infusion devices and the respective patients may be established at each infusion device, sent to the infusion management server (IMS) where association information is stored and managed. In addition, the infusion management system includes at least one infusion device (most often, a plurality of infusion devices). The infusion device has the capability to query the infusion management server (IMS) for medication orders, present a list of non-administered orders to a user in a selectable format on a display screen of the infusion device, and then use the properties of the selected order to automatically program infusion settings for administration of medication.

In some embodiments, upon the start of delivery for a programmed infusion, the infusion device notifies the infusion management server (IMS). As a result, the infusion management server (IMS) removes the associated order from the list of pending order administrations. Multiple infusion devices can be associated with the same patient.

Upon notification that an order has been administered, this information is made available to other infusion devices associated with the same patient, which prevents that order from being select on that order any other infusion device.

Accordingly, the infusion management system disclosed herein provides users with a system that enables simple and efficient administration of infusion devices and therefore medication for a patient. Prior to discussing the technology in greater detail, some concepts are now introduced.

As discussed herein, the term "automatic" generally refers to performance of a process where at least one step requiring human interaction has been eliminated or the level of human interaction has been substantially reduced. The term "automatic" is not meant to imply complete elimination of human interaction. For example, in some instances, it is desired to have human interaction to ensure appropriate error checking and to affirm proper operation prior to advancement of the process. Accordingly, it is considered that semi-automatic, partially automated and other such processes may be considered as automatic or automated, in at least some instances.

As discussed herein, the term "medication" generally refers to any substance that is to be administered to a patient according to the direction of a caregiver. Examples of medication include medicine administered for diagnostic or therapeutic purposes, liquids such as those providing nutrition or hydration and any other similar substance. Generally, medication administered as disclosed herein is fluidic and suited for administration with an infusion device.

As discussed herein, the term "infusion device" generally refers to a device that includes components appropriate for dispensing fluids such as those that contain medication to the patient. Exemplary components of an infusion device include, without limitation, a pump, a power supply, an inlet, an outlet, at least one valve, and the user interface. Additional components may include a processor, memory, data storage, a screen (such as one providing a graphical user interface), and at least one type of network interface. Non-limiting examples of a network interface include: wired interfaces (such as Ethernet, USB and the like); wireless interfaces (such as Wi-Fi implementing 802.11 protocol, Bluetooth, near field communications (NFC), and the like); and, optical interfaces (such as an infrared port, a fiber port, and the like). The infusion device may be outfitted with additional components such as a barcode reader, a radio frequency identification (RFID) interface and the like. The infusion device may implement machine executable instructions stored on machine readable media, in order to execute a method. The machine executable instructions may be referred to as "software." Functionality of the infusion device is not necessarily contained within a single box or discrete device. For example, software used to control the infusion device may be accessed through the network interface.

The infusion device may be configured for providing medication in any manner deemed appropriate. For example, the infusion device may be configured to provide medication on a continuing basis, an intermittent basis, a demand basis, according to a predetermined profile, or in some combination of the foregoing. The infusion device may be configured to pump large volumes, such as volumes of nutrients and/or fluid. The infusion device may be configured to pump small volumes, such as volumes of hormones or anesthetics. The infusion device may be configured with any type of pump deemed appropriate. For example, the infusion device may make use of a peristaltic pump, a screw, a pressurized bag, a gravity feed or any other type of device that may urge the dispensing of the medication.

The infusion device may be configured with a variety of redundant features. For example, the infusion device may be configured with redundant power supplies including main and backup batteries, processors, and other such components. Software used to operate the infusion device may be configured with features that require double checking and other aspects designed to overcome or address human factors issues.

A variety of aspects of the infusion device may be internally adjusted through a controller (e.g., an onboard and/or remote processor). For example, the delivery mechanism, communications, system monitoring and the like may be controlled via the controller. Accordingly, these aspects and others may be controlled through implementations of software. As discussed herein, the terms "order" and "order objects" are closely related. Accordingly, one is not to be construed as exclusive of the other, and in some embodiments, the order and the order object may be identical. Generally, the term "order" is used to signify a prescribed order for medication to be given to a patient, while the term "order object" is used to signify a translation of the prescription into a form that is usable or consumable by a given infusion device. The order object is used to inform the infusion device how it should be programmed in order to deliver the respective order.

Turning now to FIG. 1, aspects of an exemplary infusion management system 5050 are shown. In general, the infusion management system 50 includes an infusion management server (IMS) 10 that communicates with a respective infusion device 5. In this example, the infusion management server (IMS) 10 receives information from systems contained within an enterprise 20.

As an overview of the infusion management system 50, it may be considered that the infusion management server (IMS) 10 receives orders 6 from the enterprise 20. Alternatively, the infusion management server (IMS) 10 may have a separate interface for receiving orders 6. The infusion management server (IMS) 10 will assemble appropriate information and format order objects 7 from the orders 6. The order objects 7 are then communicated to a respective infusion device 5. The infusion device 5 is used to administer the medication to the patient. The infusion device 5 may communicate device status information 8, as well as other information such as a request, to the infusion management server (IMS) 10. The infusion management server (IMS) 10 may analyze the device status information 8 and provide analysis results. Additionally, the infusion management server (IMS) 10 may forward the device status information 8 upstream to the enterprise 20. Generally, information communicated from the infusion management server (IMS) 10 to the enterprise 20 is communicated as system status information 9.

Generally, the infusion management server (IMS) 10 includes computing resources as necessary or appropriate for enabling functionality described herein. For example, the infusion management server (IMS) 10 may include one or more servers, at least one user interface, zero or more networked personal computers, tablets or other personal computing devices, a variety of computing interfaces, and other such features. The infusion management server (IMS) 10 may include machine executable instructions stored on machine readable media, in order to execute a method. The machine executable instructions may be referred to as "software."

Generally, the term "enterprise" 20 refers to computer systems, networks, and other devices that are presently available in a healthcare environment, and it may be relied upon to interface, at least in part, with the infusion management system 50. Generally, at least one component of the enterprise 20 may be configured to communicate information to the infusion management server 10 and to access information available elsewhere within the enterprise 20. Exemplary information maintained by the enterprise 20 patient profile information, comprehensive medical records, diagnostic information, therapeutic information, insurance information, caregiver profile information, and other similar information. The enterprise 20 may include other connections to or communications with specialized equipment such as imaging apparatus, lab equipment, remote interfaces and the like. The enterprise 20 may also include information on privileges for system users and may implement security features for controlling access to features of the enterprise 20 and/or infusion management system 50. Accordingly, the enterprise 20 may include machine executable instructions stored on machine readable media, in order to execute a method. The machine executable instructions may be referred to as "software."

Exemplary systems within the enterprise 20 that may be used to generate a medication order 6 include, for example, a variety of systems including, but not limited to: Computerize Physician Order Entry (CPOE) systems; Pharmacy Information Systems (PIS); and electronic Medication Administration Record (eMAR) systems.

As a matter of convention, and for purposes of discussion, it may be considered that the enterprise 20 provides medication information as an order 6 to the infusion management server (IMS) 10. Generally, the order 6 includes such information as a name brand of medication and a particular dosing protocol. The order 6 may have been ordered by a doctor, nurse practitioner, or other qualified personnel, and is designated for a particular patient.

In some embodiments, the infusion management server (IMS) 10 receives the prescription 6 from the enterprise 20. Once received, the infusion management server (IMS) 10 may do a variety of things with the order 6. Exemplary tasks performed by the infusion management server (IMS) 10 include deriving an order object 7 from the order 6. The order object 7 generally includes a format for the infusion device 5 that is recognizable to the components therein (such as a processor within the infusion device 5). Accordingly, the infusion management server (IMS) 10 may include a plurality of application programmer interface (API) modules. Generally, each one of the API modules contains configuration information for each type of infusion device 5 that is maintained within the infusion management system 50. By using an appropriate API, the infusion management server (IMS) 10 may properly format a given order 6 into an order object 7 for the respective type of infusion device 5.

In some embodiments, the infusion management server (IMS) 10 is configured to receive the order 6 and make substitutions. For example, the infusion management server (IMS) 10 may be configured to provide the order object 7 with a generic version of the medication included in the order 6. Accordingly, the infusion management server (IMS) 10 may reference a substitutions database, such as one that may be accessed from systems of the enterprise 20. Adjusting the order according to a substitution requirement is one example of applying a policy (that is, and by way of example, a policy of the institution). Accordingly, it may be considered that the infusion management server (IMS) 10 may be configured to apply at least one policy with an order 6 when providing the order object 7.

The infusion management server (IMS) 10 may be configured to provide updates to existing orders 6 and indicate when an order 6 has been administered.

In one non-limiting embodiment, as orders 6 arrive, the orders 6 are transformed into order objects 7 and stored by the infusion management server (IMS) 10. As updates to orders 6 are received, these updates are applied and stored by the infusion management server (IMS) 10 as well. Changes may include, but are not be limited to, one or more changes to the order 6, an indication that the associated medication has been dispensed by the pharmacy or an indication that a care provider has administered the associated medication.

In one embodiment, a caregiver initiates programming of an infusion device 5 at a local interface, such as on a front of the infusion device 5. Either prior to or as part of the programming process, the user may optionally indicate the patient for whom the administration is being delivered.

In some further embodiments, the infusion device 5 may send a request to the infusion management server (IMS) 10 for all outstanding (i.e. not already administered) orders 6 for a patient that is associated with the infusion device.

Additionally, the user may request information on any orders 6 directed to that infusion device 5. In one embodiment, the order object 7 that are derived from the orders 6 contain the associated program settings for the infusion device 5 and indicate actions need to be taken for each order 6 that may be selected. For example, order objects 7 may include a plurality of settings for parameters such as: infusion rate, dose, concentration, duration, dose rate, volume to be infused, the drug name and advisory information.

If start time is imminent for a given order 6, the infusion device 5 can use the associated order object 7 (e.g., information indicating the fluid to be injected into the respective patient) to auto-program itself. If multiple order objects 7 are available, they can be presented to a user operating the infusion device 5 in a selectable format. The user may optionally select one of the returned order objects 7 or choose to manually program the infusion device 5 to deliver one or more fluids to a respective patient. Once selected, the infusion device 5 will use that order object 7 to automatically program itself. In some embodiments, the infusion device 5 and then ask the user to confirm those settings before administering the infusion.

In one embodiment, once programmed, an association exists between the infusion device 5, the patient, the order 6 and the programmed infusion. A user may choose to accept and confirm the settings, modify those settings, or even disassociate the order with the administration all together.

All user actions can be maintained in an audit history as a way of tracking how the care provider chose to administer the infusion and its relationship with an order 6. Upon the completion of the infusion, this information and an indication that the order 6 was administered is sent to the infusion management server (IMS) 10. The infusion management server (IMS) 10 may optionally publish the audit information and the updated order status to any interested consumers within the healthcare enterprise via an outbound interface.

Any subsequent changes to the infusion, such as drug titration, may be made through direct manipulation of the program settings on the infusion device 5. These changes may also be maintained in an audit history which continues to be associated with the initiating order 6.

The infusion management server (IMS) 10 may be configured to take into account other aspects of patient care. For example, the infusion management server (IMS) 10 may be configured to adjust delivery of medication according to external factors such as co-delivery of other medication by another infusion device 5. Generally, the infusion management server (IMS) 10 works in conjunction with technology provided through the enterprise 20 provide for such functionality, although this is not a requirement.

Generally, the infusion management server (IMS) 10 provides order objects 7 to the infusion device 5 in a format that is appropriate for the respective infusion device 5. The infusion device 5 may return information such as device status information 8 to the infusion management server (IMS) 10. Device status information 8 may include acknowledgment of the order object 7. As an example of a fail-safe mechanism, a particular order object 7 received by the infusion device 5 may be returned to the infusion management server (IMS) 10 as part of the device status information 8. At this point, the infusion management server (IMS) 10 may perform a comparison of the order 6 that was sent to the infusion device 5 and order objects 7 that were received from the infusion device 5. If there is not a perfect agreement (that is, parity) between the order 6 and order object 7, the infusion management server (IMS) 10 may alert the caregiver through the user interface on the infusion device 5 until the caregiver appropriately addresses any disparity.

Similarly, the infusion management server (IMS) 10 may provide information such as system status information 9 to the enterprise 20. For example, the infusion management server (IMS) 10 may be configured to track a plurality of infusion devices 5. Accordingly, and by way of example, the infusion management server (IMS) 10 may provide system status information 9 to the enterprise 20, where the system status information 9 includes device status information 8 for any given infusion device 5 and/or group of infusion devices 5. The system status information 9 may include group information such as, for example: percent capacity of usage of infusion devices 5 within the infusion management system 50; include tracking and locating information for each infusion device 5; may provide calibration records and maintenance scheduling for infusion devices 5 and other such information as deemed appropriate. Generally, the system status information 9 may include device status information 8 and may further include system information that is useful for managing the infrastructure that is supportive of the infusion management system 50.

The device status information 8 and the system status information 9 may be parsed in any manner deemed appropriate. For example, capacity of usage may be determined according to usage of all infusion devices 5 within the infusion management system 50. As another example, capacity of usage may be determined according to a given criteria such as usage within a care unit, a work shift, by device type and by other similar criteria. In short, device status information 8 and system status information 9 may be combined to provide substantial insight into operation of the infusion management system 50, performance of the infusion management system 50 and insight into patient care and medication administration.

Both device status information 8 and system status information 9 may incorporate appropriate information for enhancing operation of the infusion management system 50. For example, the device status information 8 may include information regarding administration of medication. Additionally, the device status information 8 may include device specific information regarding the infusion device 5. For example, the device status information 8 may feedback to the infusion management server (IMS) 10 condition of a battery (for example, when the infusion device 5 is being powered by an internal battery).

As one might imagine, order objects 7 are not necessarily limited to medication information. For example, the information management server (IMS) 10 may provide information to the infusion device 5 that includes related demographic information or semantic information. For example, the order objects 7 that are provided to the infusion device 5 may include date, time, location information, attending physician, patient name, patient age, and other such information as deemed appropriate by a user, designer or manufacturer or other similarly interested party.

In some embodiments, the infusion device 5 may be configured to retain additional dynamic device information, which may also be provided as device status information 8. Dynamic device information may be provided to the infusion management server (IMS) 10 to enhance management of the infusion device 5 as well as administration of medications to the patient. Exemplary and non-limiting dynamic device information includes: records of administrations by a designated infusion device 5, (which, may in turn include information such as each associated order object 7, or a summary thereof); a user history table; a location history table; a table of device state information; calibration information and, any similar information deemed appropriate by a user, designer or manufacturer or other similarly interested party.

Having explained some of the additional information that may be included in the device status information 8 and the system status information 9, it should be understood that the term "device status information" and "system status information" generally signify information that is provided or flows "upstream" in the infusion management system 50. That is, device status information 8 is not necessarily limited to containing only device status information, and/or may include additional information that is related to the infusion device 5 or the administration of medication to a patient. Similarly, as a matter of convention, it may be considered that the order 6 and the order objects 7 flow "downstream" to the patient.

Other types of information may be communicated between the infusion device 5, the infusion management system (IMS) 10 and the enterprise 20. For example, requests may be pushed or received upstream or downstream in the infusion management system 50. Requests may be initiated, for example, to obtain device status information 8 and/or system status information 9. Requests may be initiated for any type of information deemed appropriate by a user, designer, manufacturer or other similarly interested party.

Communication of the order 6, the order object 7, device status information 8, and system status information 9 may be performed on a real time, substantially real time, or near real-time basis. That is, communications of the foregoing may occur in a manner that is rapid enough to permit a caregiver to administer the infusion management system 50 appropriately to manage care of the patient in a way that is deemed to meet an existing standard of care for a given protocol. That said, it is not required that communication of any one of the order 6, the order object 7, the device status information 8, and the system status information 9 be communicated in such a rapid fashion. Again it is merely required that communications are adequate for a caregiver to perform the desired tasks.

Generally, the infusion management system 50 is configured to perform tasks on at least one of a semi-automated and an automated basis. That is, the infusion management system 50 is configured to perform tasks on the basis that minimizes human intervention. Accordingly, the infusion management system 50 provides for error reduction when compared to prior art systems, and use of personnel for other tasks associated with caregiving.

Communications between the enterprise 20, the infusion management server (IMS) 10 and the infusion device 5 may be performed in any manner deemed appropriate. The infusion management server (IMS) 10 may provide multiple communication services. The communication services enable communications amongst various infusion devices 5 and other computer systems within the enterprise 20. The services can include one or more different types of communication mechanisms. For example, one service may be capable of communicating using RESTful web services while another, performing the same function, may support a TCP sockets based communications protocol, and so on. In one non-limiting example embodiment, the infusion management server (IMS) 10 communicates, using encrypted messaging, with the infusion device via a secure HTTP (i.e., HTTPS) protocol, ensuring that communication and the connection between the infusion management server (IMS) 10 and the infusion device 5 is secure and that messages are fully encrypted.

The infusion management server (IMS) 10 may operate on a local area network (LAN) that is public (i.e., a non-dedicated system). In one embodiment, the infusion management server (IMS) 10 is configured for communicating with infusion devices 5 connected either directly or wirelessly to the public LAN. In some embodiments, the infusion management system 50 is operated on an independent network that is dedicated to the infusion management system 50. In some further embodiments, the infusion management system 50 is operated on an independent or dedicated network, while retaining the public LAN as a backup communications system.

In summary, the infusion management system 50 provides institutions and caregivers with robust capabilities for managing delivery of medication that is dispensed by an infusion device 5.

Figure 2:
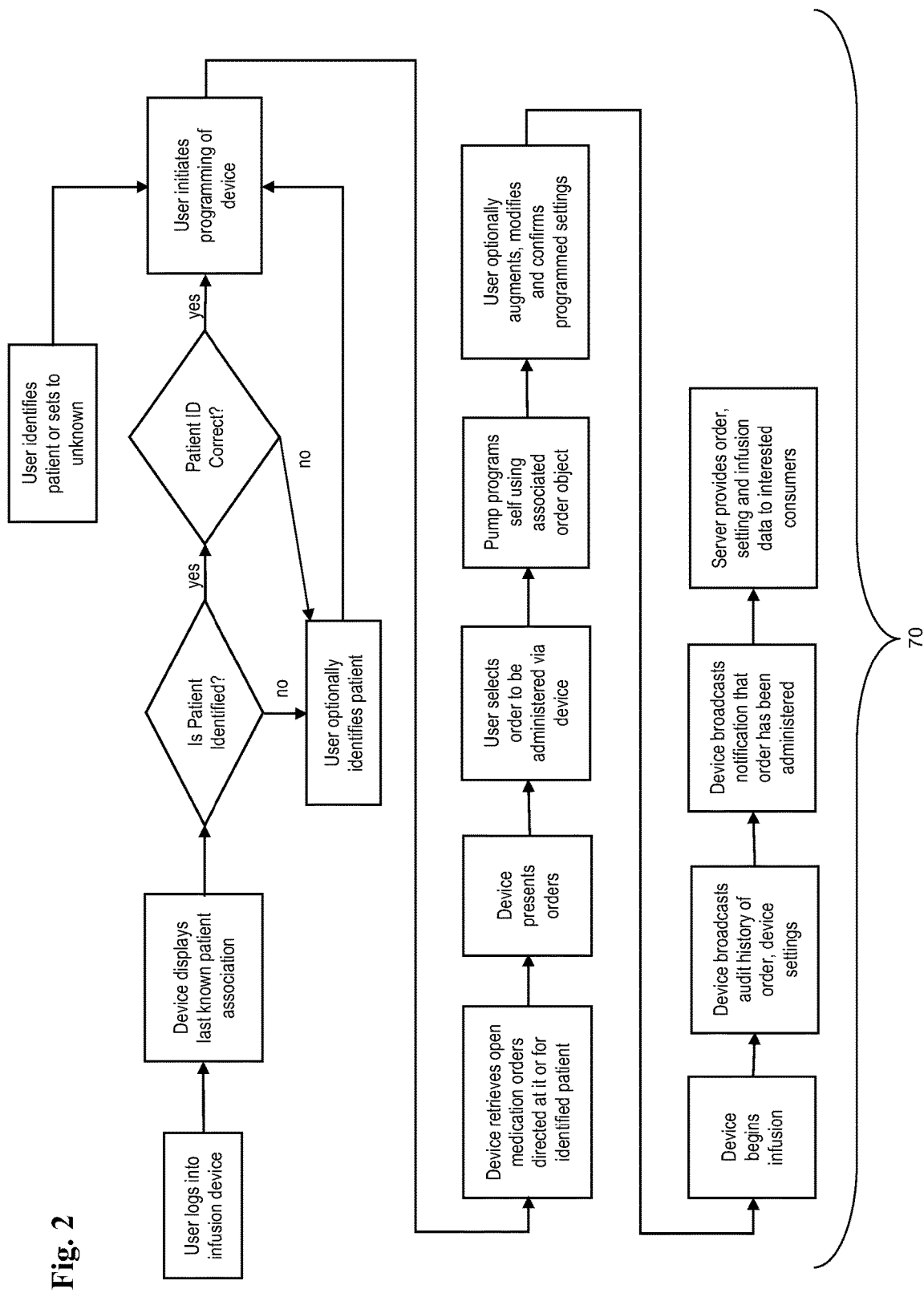
FIG. 2 is a flow chart providing an exemplary protocol for use of the infusion management system depicted in FIG. 1; and, FIG. 3 is a flow chart depicting aspects of a computing infrastructure, where at least some of the associated components are suited for use in the infusion management system depicted in FIG. 1.

Referring now to FIG. 2, there is shown a flow chart that depicts aspects of an exemplary protocol 70 for use of the infusion management system 50. As an overview, the exemplary protocol 70 generally includes logging into the infusion device and associating a patient with the infusion device. During setup, a user may log into the infusion device manually (such as by a keypad and/or graphical user interface (GUI)), or automatically (such as through RFID recognition or barcode scanning of the user by the infusion device). The infusion device may display the last known patient association (that is, the identity of the last patient served by the infusion device). If the patient is incorrectly associated with the infusion device, the user may associate a new patient with the infusion device. Association of the new patient may be performed manually (such as by a keypad and/or graphical user interface (GUI)), or automatically (such as through RFID recognition or barcode scanning of the patient by the infusion device). Once the user has verified the infusion device is properly associated with a given patient, initial setup has been completed.

Once the initial setup has been completed, the infusion device will retrieve orders associated with the patient, or for the specific device. The infusion device presents the orders to the user. User then selects the appropriate order for administration. Using the selected order, the infusion device sets internal parameters such as delivery rate, delivery volume and the like. In some embodiments, the user is provided with options to adjust the settings established by the automatic configuration by the infusion device. Additionally, the user may set optional parameters such as alarm settings and the like. Once setup has been completed, the user can initiate infusion. Subsequently (and/or during the infusion), the infusion device may store and/or broadcast relevant information about the infusion. The relevant information may be provided locally, such as on an interface of the infusion device, and/or provided as device status information and forwarded to the infusion management server (IMS).

Having thus introduced the infusion management system 50, some additional aspects and embodiments are now presented.

The infusion management system 50 includes substantial capacity and flexibility. Accordingly, a variety of additional features, modes of use protections and limitations may be realized.

As one example of a system protection, the infusion device 5 may be configured such that once programmed the infusion device 5 may optionally query the infusion management server (IMS) 10 to determine the status of other infusions being delivered to the same patient and the medication and settings associated with that infusions. If any conflict exists between the infusion being programmed and any other infusion being administered to the same patient, a warning will be presented to the device operator.

In some embodiments, if a respective order 6 has a scheduled start time in the future, the device operator may be given the option to start the infusion immediately or at the scheduled time.

In some embodiments, such as those where repeated administration of a given medication will take place, the device operator may be given the option to recall a specific order object 7 for the future administrations.

The infusion device 5 may be configured such that a user may electronically scan at least one of a patient identification bracelet, a medicine container or other item to call up a specific order object 7. For example, once a respective infusion device 5 has been associated with a given patient, the user may scan a barcode on a bag of fluid, and the infusion management system 50 will automatically programmed the infusion device 5 to correlate to an associated order object 7 for that patient.

In some embodiments, an infusion device 5 is established for remote operation. For example, in infusion device 5 may be set up in the home of a patient and configured to communicate with the infusion management server (IMS) 10 over the Internet using a secure HTTPS connection. Despite the infusion device 5 being established at a remote location, the infusion management system 50 may provide the infusion device 5 with a variety of capabilities such as those described elsewhere here in.

In some other embodiments, the infusion device 5 includes retrofit of a prior art infusion device. An appropriate retrofit kit (not shown) may be used to configure the prior art infusion device for operation within the infusion management system 50. The retrofit kit may include, for example, a processing unit configured for communicating with the prior art infusion device (such as through an existing communications port on the prior art infusion device). The processing unit may include, for example, a user display, as well as software for communicating with the infusion management server (IMS) 10 and commanding the prior art infusion device appropriately.

An exemplary device that includes many of the components appropriate for use as a processing unit of a retrofit kit includes a smart phone. Accordingly, use of a device such as a smart phone may provide enhanced flexibility with additional communications channels, additional commercially available software, and the like.

Generally, implementations of "software" as discussed herein include machine executable instructions stored on machine readable media as a non-transitory signal. Embodiments of software may be programs in any language deemed appropriate. Generally, implementations of software provided herein include objects that are defined using eXtensible Markup Language (XML). However, the software provided herein may be defined in any manner deemed appropriate. For example, other tools for platform independent software may be used. Combinations of software languages, compilers and other development tools may be used. Other types of development tools include scripting languages, integrated development environments, build tools and a variety of other types of tools. At least a portion of the software may be implemented as "firmware." That is, at least a portion of the software may be provided in read only memory. Exemplary aspects of the infusion management system that may be implemented as firmware include portions relating to authentication and security.

Figure 3:
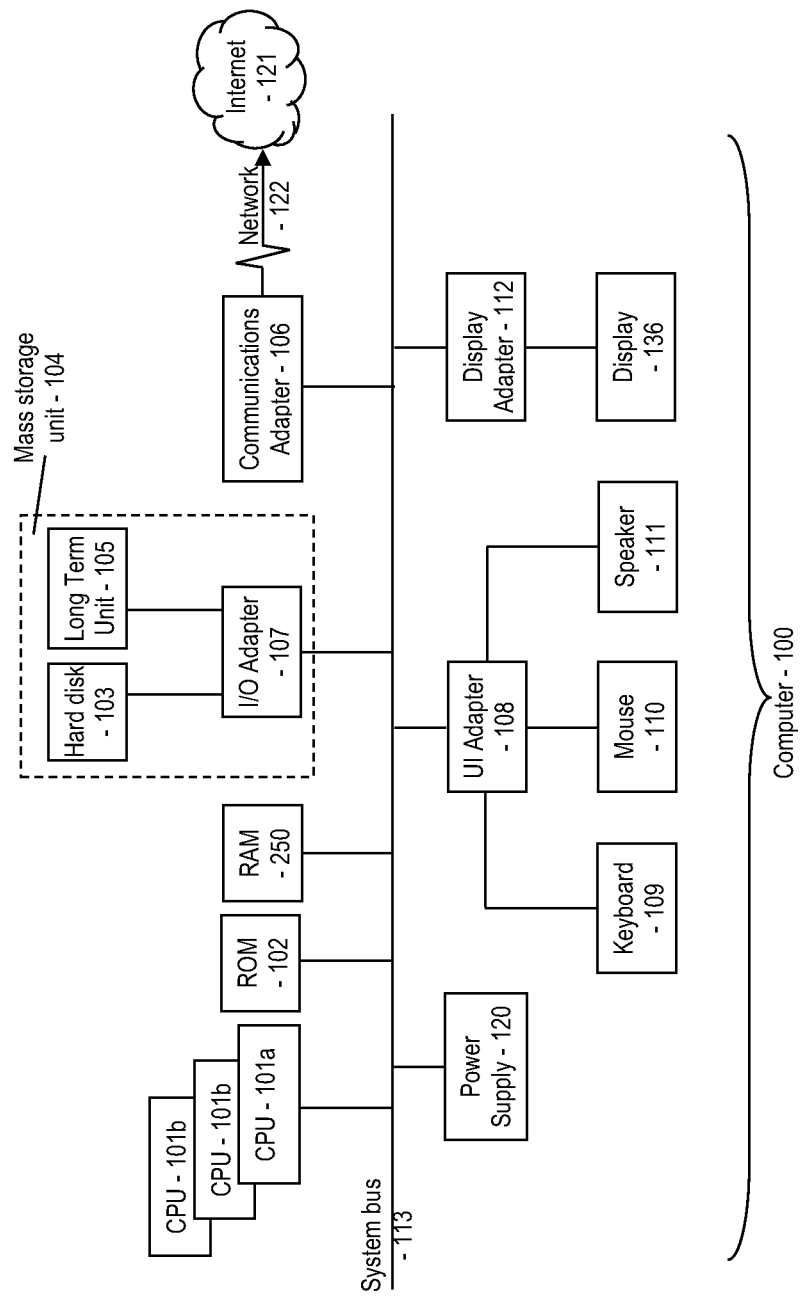

Software, firmware, and other components as described herein may rely upon a computer, a computing network and other such technologies. Exemplary aspects of a computing environment are depicted in FIG. 3. At least some of the aspects depicted in FIG. 3 may be implemented in a respective infusion device, a retrofit for a prior art infusion device, the infusion management server, or as are otherwise deemed appropriate.

Referring now to FIG. 3, exemplary aspects of a computer 100 are depicted. Computer 100 has one or more central processing units (processors) 101*a*, 101*b*, 101*c*, etc. (collectively or generically referred to as "processor(s)" 101). Processors 101 are in communication with system memory 250 and various other components via a system bus 113. Read only memory (ROM) 102 is in communication with the system bus 113 and may include a built-in operating system (BIOS), which controls certain basic functions of computer 100. Additionally, the system bus 113 may provide power to the processor 101, system memory 250, and read only memory 102.

FIG. 3 further depicts an input/output (I/O) adapter 107 and a communications adapter 106 coupled to the system bus 113. I/O adapter 107 may be a parallel ATA (PATA, also called IDE or EIDE), Serial ATA (SATA), SCSI, Serial Attached SCSI (SAS), optical adapter such as fiber channel, or include any other type of interface deemed appropriate. The I/O adapter 107 generally provides for communicating with a hard disk 103 and/or long term storage unit 105 (such as a tape drive) or any other similar component (such as an optical drive). I/O adapter 107, hard disk 103, and long term storage unit 105 (and other similar components as may be included) are collectively referred to herein as mass storage 104.

A communications adapter 106 interconnects system bus 113 with an outside network 122 enabling computer 100 to communicate with other systems such as the enterprise 20. The communications adapter 106 may be supportive of at least of one of wired and wireless communication protocols. For example, the communications adapter 106 may support protocols such as wired Ethernet, wi-fi (e.g., 802.11 protocols), UMTS, dial-up, active-sync, cellular (using protocols such as, for example, GSM, GPRS, EDGE, CDMA, TDMA, 3G, 4G, and the like). Generally, the communications adapter 106 communicates with a network 122, and may communicate (directly or indirectly) with the Internet 121.

The computer 100 is powered by a suitable power supply 120. In some embodiments, the power supply 120 includes at least one transformer for receiving alternating current (AC) and transforming the AC into a suitable form of direct current (DC). In other embodiments, the power supply 120 includes at least one battery. The power supply may include appropriate circuitry for receiving and controlling various forms of input power.

Input/output devices are shown as connected to system bus 113 via user interface (UI) adapter 108. A keyboard 109, a pointing device (e.g., a mouse) 110, and speaker 111 may be included and interconnected to system bus 113 via user interface adapter 108. Other user interface components may be included as deemed appropriate.

A display adapter 112 connects display monitor 136 is connected to system bus 113. The display adapter 112 and/or display monitor may be configured with various components, such as a graphics adapter to improve the performance of graphics intensive applications, a video controller, a capacitive (i.e., touch screen) display, and the like.

In some embodiments, adapters 106, 107, 108 and 112 may be connected to one or more I/O busses that are connected to system bus 113 via an intermediate bus bridge (not shown). Suitable I/O buses for connecting peripheral devices such as hard disk controllers, network adapters, and graphics adapters may include common protocols, such as the Peripheral Components Interface (PCI) bus.

Generally, the computer 100 stores machine readable instructions on machine readable media (such as in ROM, RAM, or in the mass storage unit 104). The machine readable instructions (referred to herein as "software," as an "application," as a "client, a "process," a "plug-in" and by other similar terms) generally provide for functionality as will be discussed in detail further herein.

Some of the machine readable instructions on machine readable media may include an operating environment. For example, and as presented herein, a suitable operating environment is WINDOWS (available from Microsoft Corporation of Redmond Wash.). Software as provided herein may be developed in, for example, SQL language, which is a cross-vendor query language for managing relational databases. Aspects of the software may be implemented with other software. For example, user interfaces may be provided in XML, HTML and the like.

The computer 100 may include, or exclude, as appropriate, the foregoing components and other components. For example, other components such as routers, bridges, firewalls, switches, servers, middleware and other components may be available.

In some embodiments, the computer 100 may be designed and configured for stationary operation, while in some other embodiments the computer 100 is designed and configured for mobile operation. Some exemplary embodiments of commonly available mobile computers 100 that may be suited for practice of the teachings herein include laptops, smart-phones, tablets and the like.

A computing system may include a plurality of computers 100. For example, in the system, at least one computer 100 in the plurality may include substantial storage, memory, processors, mass storage and the like. Generally, such a configuration may be useful as the infusion management server. At least one computer 100 in the plurality may be designed with mobility as a primary purpose. For example, memory may replace a hard disk due to a physically compact nature of the memory. Generally, such a configuration is useful as a "mobile computer," a "mobile station" or by other similar terms. Such latter embodiments may be useful in support of the infusion devices.

A particular computer 100 in a computing system may be purpose-oriented. For example, a computing infrastructure may use one computer 100 principally as the infusion management server (IMS) 10, and a plurality of other computers as input devices (e.g., as infusion devices 5 configured for being operated remotely by users for interfacing with the computing infrastructure), as a console (e.g., a dedicated system for managing the computing infrastructure), and the like.

It should be recognized that some functionality as may be described herein may be implemented by hardware (such as by the foregoing components), or by software, as appropriate. Accordingly, where reference is made to implementation in one manner or another, such implementation is merely illustrative and is not limiting of techniques described. In short, the foregoing description of the computer 100, and systems making use of or incorporating the computer 100, merely provides an environment for the teachings herein and is not to be construed as limiting, but as illustrative of aspects of the computer 100 and systems that incorporate the computer 100.

Various other components may be included and called upon for providing for aspects of the teachings herein. For example, additional materials, combinations of materials and/or omission of materials may be used to provide for added embodiments that are within the scope of the teachings herein.

When introducing elements of the present invention or the embodiments thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method comprising:
   via computer processor hardware, executing operations of:
   receiving a medical infusion order at an infusion management server operable to manage the medical infusion order;
   receiving a retrieval request at the infusion management server, the request received from a first infusion device, the retrieval request comprising a request for retrieval of one or more available medical infusion orders;
   transmitting a message including the medical infusion order from the infusion management server over a network to the first infusion device, wherein the first infusion device is operable to automatically establish infusion settings for administration of medication based on one or more order objects included in the medical infusion order;
   at the infusion management server, receiving confirmation from the first infusion device that the medical infusion order has been completed in which the medication has been administered by the first infusion device to a recipient;
   at the infusion management server, updating an infusion order list of one or more pending non-administered medical infusion orders to remove the medical infusion order from the infusion order list and to denote that the medical infusion order is no longer pending;
   providing a notification to a set of at least one infusion device other than the first infusion device, the notification indicating that the medical infusion order has been administered to the recipient, the notification preventing the medical infusion order from being selected for delivery to the recipient; and
   providing the updated infusion order list to the set of at least one infusion device.

2. The method as in claim 1, wherein the first infusion device is operable to display a graphical user interface on a display screen of the first infusion device.

3. The method as in claim 1, wherein the first infusion device is operable to:
receive the medical infusion order over the network from the infusion management server;
associate the medical infusion order with the recipient, the recipient being a patient; and
adjust at least one setting of pumping fluid from the first infusion device to the patient according to the one or more order objects included in the medical infusion order.

4. The method as in claim 3 further comprising:
transmitting an identity of the recipient from the infusion management server to the first infusion device.

5. The method as in claim 1, wherein the first infusion device displays a graphical user interface when the medical infusion order is being administered to the recipient, the recipient being a patient.

6. The method as in claim 1, wherein the medical infusion order controls delivery rate, times and volumes of fluid being administered from the first infusion device to the recipient.

7. The method as in claim 1 further comprising:
at the infusion management server, receiving a communication from the first infusion device indicating that the infusion device has started delivery of a fluid, as specified by the medical infusion order, to the recipient.

8. The method as in claim 7 further comprising:
in response to receiving the communication at the infusion management server, removing the medical infusion order from the infusion order list of pending at least one medical infusion orders assigned to the recipient, the recipient being a patient.

9. The method as in claim 1 further comprising:
at the infusion management server:
receiving status information from the first infusion device indicating that the first infusion device has received the one or more order objects associated with the medical infusion order, wherein the status information comprises one or more of the order objects;
comparing the received one or more order objects to one or more order objects that were sent to the first infusion device as part of the medical infusion order to identify whether there is parity between the compared order objects; and
when there is not parity between the compared order objects, creating an alert to be displayed on a display screen of the first infusion device.

10. The method as in claim 1, wherein each of the order objects comprises information indicating: i) a medication infusion start time, ii) a medication infusion rate, and iii) a medication infusion duration.

11. A method comprising:
via computer processor hardware, executing operations of:
transmitting from a first infusion device to an infusion management server, a retrieval request requesting retrieval of any available medical infusion orders assigned to the first infusion device;
at the first infusion device, receiving over a network from the infusion management server one or more medical infusion orders assigned to the first infusion device;
initiating a display of the one or more medical infusion orders as a an infusion order list displayed on a display screen of the first infusion device;
performing a selection of a medical infusion order from the infusion order list on the display screen;
automatically establishing infusion settings at the first infusion device for administration of medication based on one or more order objects included in the medical infusion order;
controlling the first infusion device to deliver fluid as specified by the selected infusion order amongst multiple medication orders displayed on the display screen;
via the infusion management server, updating the infusion order list to remove the medical infusion order and to denote that the medical infusion order is no longer pending; providing the updated infusion order list from the infusion management server to a set of at least one infusion device other than the first infusion device, to denote the medical infusion order has been administered; and
providing a notification to the set of at least one infusion device other than the first infusion device, the notification indicating that the medical infusion order has been administered, the notification preventing the medical infusion order from being selected for delivery to the recipient.

* * * * *